United States Patent
Fiato

(10) Patent No.: US 8,148,435 B2
(45) Date of Patent: Apr. 3, 2012

(54) INTEGRATED COAL TO LIQUIDS PROCESS AND SYSTEM

(75) Inventor: Rocco A. Fiato, Basking Ridge, NJ (US)

(73) Assignee: Accelergy Corporation, Houston, TX (US)

(*) Notice: Subject to any disclaimer, the term of this patent is extended or adjusted under 35 U.S.C. 154(b) by 392 days.

(21) Appl. No.: 12/470,072

(22) Filed: May 21, 2009

(65) Prior Publication Data

US 2009/0286889 A1 Nov. 19, 2009

(30) Foreign Application Priority Data

| Nov. 16, 2007 | (CN) | 2007 1 0186415 |
| Nov. 14, 2008 | (CN) | 2008 1 0182143 |
| Nov. 14, 2008 | (WO) | PCT/CN2008/073073 |

(51) Int. Cl.
$C07C\ 27/00$ (2006.01)

(52) U.S. Cl. ......... 518/706; 518/700; 518/702; 518/705

(58) Field of Classification Search ............... 518/700, 518/702, 705, 706
See application file for complete search history.

(56) References Cited

U.S. PATENT DOCUMENTS

| 4,211,631 A * | 7/1980 | Carr et al. ............ 518/702 |
| 4,277,416 A * | 7/1981 | Grant ............... 518/703 |
| 4,332,666 A | 6/1982 | Bauman et al. |
| 4,448,665 A | 5/1984 | Zaczepinski |
| 4,485,008 A | 11/1984 | Maa et al. |
| 5,198,099 A | 3/1993 | Trachte et al. |
| 5,200,063 A | 4/1993 | Neskora et al. |
| 5,338,441 A | 8/1994 | Le Viness et al. |
| 6,392,078 B1 * | 5/2002 | Ryu et al. .............. 558/277 |
| 7,271,120 B2 | 9/2007 | Sun et al. |
| 2006/0235088 A1 | 10/2006 | Olah et al. |
| 2008/0166790 A1 * | 7/2008 | Day .................... 435/262.5 |
| 2008/0190024 A1 | 8/2008 | Hobbs |
| 2008/0268302 A1 | 10/2008 | McCall |

OTHER PUBLICATIONS

Mouhua Wang, et al., Synthesis of Dimethyl Carbonate from Urea and Methanol over ZnO, Ind. Egn. Chem. Res. 2005, 44, 7596-7599, US.

Abbbas-Alli G. Shaikh, et al., Organic Carbonates, Chem. Rev. 1996, 96, pp. 951-976 US.

Yasushi Yamamoto, et al., Catalysis and characterization of Pd/NaY for dimethyl carbonate synthesis from methyl nitrite and CO, J. Chem. Soc., Faraday Trans., 1997, 93(20).

* cited by examiner

*Primary Examiner* — Jafar Parsa

(57) ABSTRACT

An integrated coal-to-liquids process is provided to minimize carbon dioxide emissions and efficiently make use of carbon resources, by recovering carbon dioxide emissions from Coal-to-Liquids (CTL) facilities, using the recovered carbon dioxide in at least one carbonylation reaction step for converting ammonia to urea and then converting urea into dimethyl carbonate.

26 Claims, 2 Drawing Sheets

INTEGRATED COAL TO LIQUIDS PROCESS AND SYSTEM

FIELD OF THE INVENTION

The present invention relates to an integrated coal-to-liquids process and system, particularly, to an integrated coal-to-liquids (ICTL) process and system in which $CO_2$ emissions are substantially reduced by converting $CO_2$ produced during the liquidation process to useful chemicals such as dimethyl carbonate or the higher alcohols.

BACKGROUND OF THE INVENTION

Increases in the cost of petroleum and concerns about future shortages has led to increased interest in other carbonaceous energy resources, such as coal, tar sands, shale and the mixtures thereof. Coal is the most important of these alternative resources for reasons including the fact that vast, easily accessible coal deposits exist in several parts of the world, and the other resources contain a much higher proportion of mineral matter and a lower carbon content. Various processes have been proposed for converting such materials to liquid and gaseous fuel products including gasoline, diesel fuel, aviation fuel and heating oils, and, in some cases, to other products such as lubricants and chemicals.

A number of problems have hampered widespread use of coal and other solid fossil energy sources that include the relatively low thermal efficiency of indirect coal-to-liquids (CTL) conversion methods, such as Fischer Tropsch (FT) synthesis and methanol-to-liquids (MTL) conversion. The conversion of coal, which has a H/C ratio of approximately 1:1, to hydrocarbon products, such as fuels that have H/C ratio of something greater than 2:1 results in at least half of the carbon in the coal being converted to $CO_2$, and thereby wasted. Additionally, the fact that a large amount of greenhouse gas (GHG), particularly in the form of $CO_2$, is emitted as a waste product in the conversion of coal to useful products has caused CTL processes to be disfavored by many from an environmental point of view.

It has been proposed to at least partially overcome the GHG problem by capturing and sequestering the carbon dioxide by re-injecting it into subterranean formations. Such an arrangement has the disadvantages of being expensive, requiring the availability of appropriate subterranean formations somewhere in the vicinity of the conversion facility, concerns about the subsequent escape into the atmosphere of the carbon dioxide, and the waste of the energy potential of the carbon content of the carbon dioxide.

The conversion of coal to valuable liquid products by indirect methods involves syngas generation. Syngas, a mixture of mainly carbon monoxide and hydrogen, can be used as a feedstock for producing a wide range of products, including liquid fuels, methanol, acetic acid, dimethyl ether, oxo alcohols, isocyanates, etc. Syngas can be generated from carbonaceous materials, such as coal, or from biomass, via gasification. It is possible to produce syngas from coal with a $H_2/CO$ ratio that is about 0.5 to about 1 using commercially available gasifiers. However, when used to produce liquid products by FT synthesis or MTL conversion, syngas with a $H_2/CO$ ratio of about 2 is desired. The $H_2/CO$ ratio of the coal produced syngas can be raised to the desired range with the water gas-shift reaction. That, however, results in large carbon dioxide emissions.

A report to the National Energy Technology Laboratory entitled "Increasing Security and Reducing Carbon Admissions of the US Transportation Sector: A Transformational Role for Coal with Biomass," DOE/NETL2007/1298, proposes reducing the amount of $CO_2$ emissions generated by gasifying coal for FT synthesis by about 20% by co-gasifying the coal with 10-15% biomass, such as a woody biomass, switchgrass, or corn stover, which have a higher $H_2/CO$ ratio. A number of problems exist with the proposed method, however. The thermal efficiency of the process is relatively low because of the energy required to gasifying coal and biomass, typically by partial oxidation, and the use of indirect FT synthesis. The required land area used to produce the biomass, and the proximity thereof to the ICTL facility, also limits the amount of biomass that can be economically employed to a maximum of about 5000 to 10,000 barrel equivalents per day. Additionally, the biomass is a substantially more expensive source of syngas than mineral carbonaceous sources such as coal, thereby adding to the product cost.

Direct coal liquefaction (DCL) methods have been developed for liquefying carbonaceous materials such as coal that have advantages in many applications to conversion by FT synthesis, including substantially higher thermal efficiency and somewhat lower $CO_2$ emissions. Such direct liquefaction methods typically involve heating the carbonaceous material and a solvent in a hydrogen containing atmosphere to a temperature in the range of about 775° to 850° F. in the presence of a catalyst, typically very finely divided iron or molybdenum or mixtures thereof, to break down the coal structure into free radicals that are quenched to produce liquid products. Hybrid coal liquefaction systems involving both direct liquefaction and FT synthesis, or direct liquefaction and biomass conversion have been proposed in which the FT synthesis or biomass conversion provides additional hydrogen for the direct liquefaction, thereby reducing carbon dioxide emissions. Hybrid coal liquefaction systems involving all three of direct liquefaction, FT synthesis, and biomass conversion have also been proposed. None of these proposed arrangements, however, achieve the combination of thermal efficiency, low cost and substantially reduced GHG emissions that would be required for them to be economically and environmentally attractive. There remains an important need for economical coal and biomass to liquids conversion processes with reduced carbon dioxide emissions and efficient use of carbon resources.

SUMMARY OF THE INVENTION

The present invention provides an ICTL process and system involving direct coal liquefaction, indirect coal liquefaction and biomass conversion processes, in which $CO_2$ generated by the coal-to-liquids processes and the biomass conversion is used as feedstock to produce algae and liquid products, such as liquid fuels and fuel additives, such that carbon dioxide emissions are minimized and carbon resources are efficiently utilized. In the indirect coal liquefaction and biomass conversion, the coal and biomass are first gasified for conversion into syngas and byproduct $CO_2$. Optionally, natural gas can also be converted to syngas by a conventional methane-steam reforming process. Portions of the syngas produced by the above processes are supplied to the direct coal liquefaction process, to an FT synthesis conversion process, and, in a preferred embodiment of the invention, to a methanol synthesis conversion process. $CO_2$ produced by the above processes is reacted with ammonia to produce urea. Methanol produced is reacted with urea to produce dimethyl carbonate (DMC) and ammonia. Ammonia from the DMC synthesis and/or from the direct coal liquefaction process is used as the ammonia for the urea synthesis.

In an alternative embodiment of the invention, instead of producing methanol from syngas for use in the production of DMC, higher alcohols are produced by the reaction of CO and H2 over a catalyst at elevated temperature and pressure.

In accordance with one aspect of the present invention, between about 70 and 90% of the coal used in the ICTL process is converted by direct coal liquefaction, and between about 10 and 30% of the coal is gasified for use in the indirect processes. Except in the case of the use of algae, all of biomass is gasified to produce syngas and byproduct $CO_2$. The biomass may be wood, straw, corncob, algae, residue from pyrolysis or hydrolysis of wood or the like, any other plant-derived material, or combinations thereof. In a preferred embodiment of the invention, the biomass includes algae produced by photosynthesis using $CO_2$ produced by the above processes and water. Optionally, a portion of the urea produced in the urea synthesis process is used as a nutrient for the algae production process. In one embodiment of the invention, if the lipid content of the algae is high enough, the algae are hydro-processed to directly convert the contained lipids to hydrocarbons. The residue of the algae hydro-processing is converted to syngas by partial oxidation. Alternatively, especially of the lipid content of the algae is lower, the algae is gasified to produce syngas. In accordance with a still further aspect of the process of the invention, a portion of the urea is stored in during time periods, such as during the nighttime, when the photosynthesis production of algae is reduced for use as a nutrient for the photosynthesis for DMC synthesis when the rate of production of algae is increased, such as during daylight hours. In this way the production of urea is a means for storing $CO_2$. Urea that is not used for producing DMC or in the growth of algae can be sold as a separate product. In accordance with a still further aspect of the invention residue from the direct coal liquefaction process is mixed and gasified with the biomass residue.

DETAILED DESCRIPTION OF EMBODIMENTS

Figure 1:
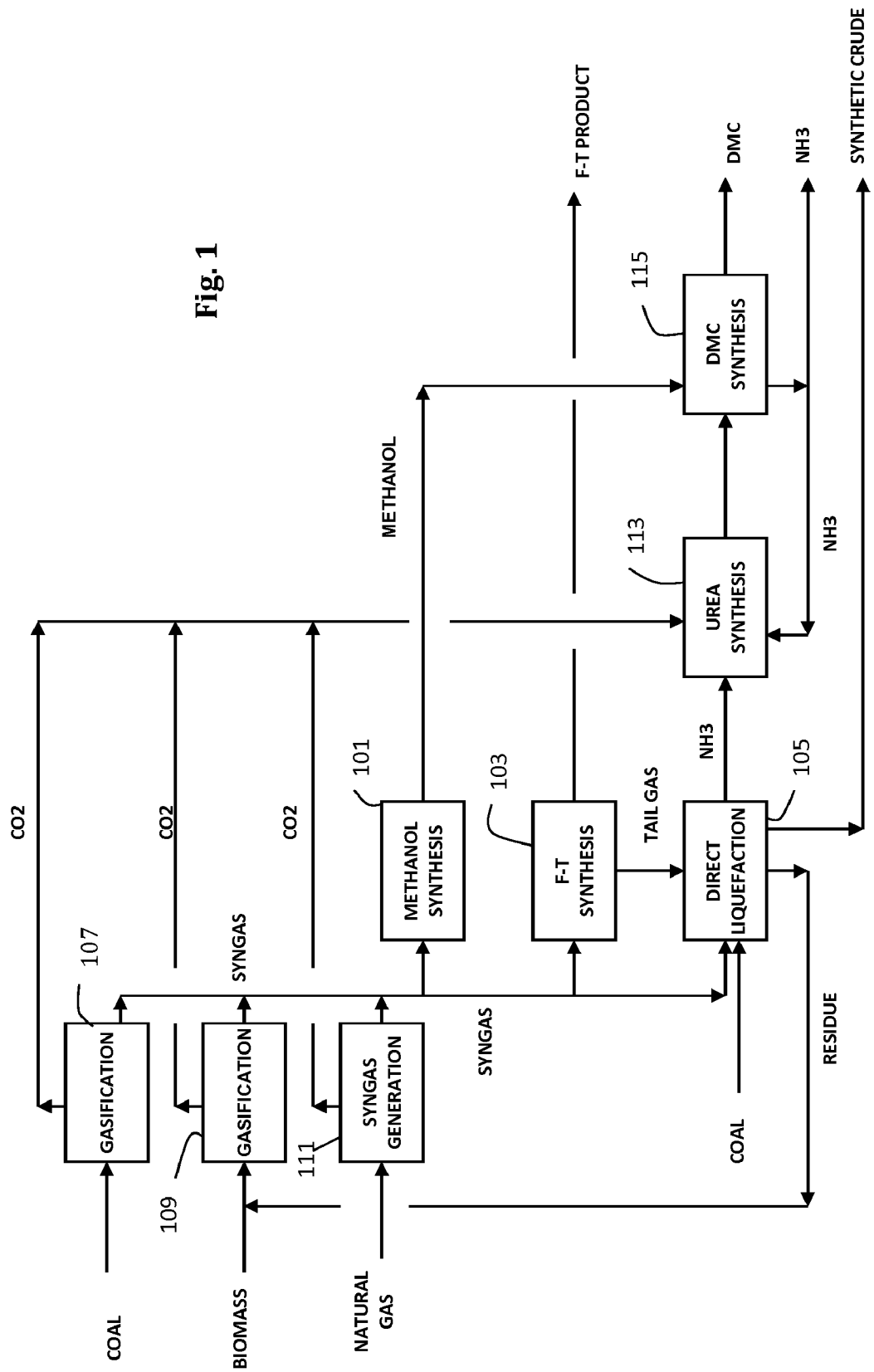
FIG. 1 is a simplified flow chart of one embodiment of an integrated coal-to-liquids process in accordance with the invention.

Various direct coal liquefaction (DCL) processes and systems have been developed, for instance those disclosed in U.S. Pat. Nos. 4,077,867, 4,485,008, 4,637,870, 5,200,063, 5,338,441, and 5,389,230, the disclosures of which are hereby incorporated by reference in their entirety. DCL processes have the advantage of being capable of substantially higher thermal efficiencies, on the order of 60-65%, than indirect processes such as FT synthesis and MTL conversion processes which are capable of thermal efficiencies of only about 45-52%. FT and DCL processes by themselves are capable of an efficiency of converting the carbon in the coal to useful products of at most about 50%. In accordance with ICTL process and system of the invention, the conversion of coal is performed primarily by DCL, with an adequate amount of coal and biomass (preferably including algae or algae hydroprocessing residue) being gasified, and optionally natural gas being converted, to produce syngas for providing additional hydrogen to the DCL process, for providing syngas to perform FT synthesis, and, in the illustrated embodiment of the invention, for producing methanol that is reacted with urea to produce DMC and ammonia. Tail gas from the FT synthesis, which includes unreacted hydrogen and CO, can be supplied to the input of the DCL for supplying additional reactants. The $CO_2$ streams produced by the DCL and indirect CTL and the biomass gasification processes are used to produce algae by photosynthesis for use as all or part of the biomass, and to produce urea through reaction with ammonia. Ammonia from the DMC synthesis can be fed back to the urea synthesis step to supply the necessary ammonia reactant. Ammonia produced by the direct liquefaction step can also be used for the urea synthesis.

It is preferable to minimize the proportion of the coal and the amount of biomass that is gasified to make syngas, both because the thermal efficiency of the indirect processes is substantially lower than that of the direct liquefaction, and because biomass, and especially algae, is relatively expensive and has limited availability. Coal gasification produces syngas with an $H_2/CO$ ratio of approximately 0.5. This ratio in the coal produced syngas can be increased by the water-gas shift reaction either in connection with the gasification more, if an iron-based catalyst is used the FT synthesis. Over 300,000 different types of algae have been discovered. All algae primarily comprise proteins, carbohydrates, fats and nucleic acids in varying proportions. Various algae types contain between about 2 and 40% fatty acids (lipids) based on their overall mass. The carbon content of algae can also vary between about 40 to 70% by atomic weight. Algae are produced by the photosynthesis reaction of $CO_2$ and water and sunlight. The algae are nourished, and the algae production facilitated, by the presence of nutrients, such as urea, in the water. Algae having higher lipids contents are more beneficial in the process of the invention but tend to grow more slowly than those having higher protein and carbohydrate contents. It is therefore often necessary to make trade-offs between the lipids content and the achievable rate of growth of the algae being used in the process. In the process of the present invention, algae such as those shown in the table below, as well as other strains with a lipid content of about 20% or more are preferred.

TABLE 1

Chemical Composition of Algae Expressed on A Dry Matter Basis (%)

| Strain | Protein | Carbohydrates | Lipids | Nucleic acid |
|---|---|---|---|---|
| Scenedesmus dimorphus | 8-18 | 21-52 | 16-40 | — |
| Chlamydomonas rheinhardii | 48 | 17 | 21 | — |
| Chlorella vulgaris | 51-58 | 12-17 | 14-22 | 4-5 |
| Spirogyra sp. | 6-20 | 33-64 | 11-21 | — |
| Prymnesium parvum | 28-45 | 25-33 | 22-38 | 1-2 |

If the lipid content of the algae is high enough, the algae are preferably hydro-processed to directly convert the contained lipids to hydrocarbons. Methods and systems for hydro-processing algae are disclosed in the published U.S. patent application US 2009/0077864 A1, the contents of which are hereby incorporated by reference. The residue of the algae hydro-processing is converted to syngas by conventional partial oxidation. Alternatively, algae can be converted to syngas by hydro-gasification or by partial oxidation. Hydro-gasification can be up to about 95% efficient in converting algae to syngas having a $H_2/CO$ ratio of up to about 3/1 or more. Algae can also be converted to syngas by partial oxidation, which results in a syngas having a lower $H_2/CO$ ratio of approximately 0.9/1. In one arrangement, the algae can first be hydro-gasified and the remaining residual material used to produce additional syngas by partial oxidation, either by itself or mixed with residual from the DCL process.

In any given instance, the optimal combinations of the percentages of direct and indirect coal liquefaction, biomass and algae gasification, direct conversion of algae to liquid fuels by hydroprocessing versus algae gasification, mixtures of bio residual and DCL residual for gasification, and other process parameters will depend on parameters such as the characteristics and costs of the individual coals, biomass and algae, market demands for particular individual products, and trade-offs between economic and environmental factors, that will vary from installation to installation and from time to time. In view of the fact that a typical commercial scale, ICTL facility costs hundreds of millions or even billions of dollars to construct and place in operation, the amount of experimentation required to determine an optical configuration of an ICTL facility in accordance with the invention is relatively modest, and would be performed in any event as part of the design and construction process for the facility in order to reduce risk.

Referring to the embodiment illustrated in FIG. 1 of the drawings, an integrated coal-to-liquids process 100 in accordance with the illustrated embodiment of the invention includes both indirect conversion of carbonaceous feeds to liquid products by means of methanol synthesis 101 and FT synthesis 103 and direct liquefaction 105 of such feeds. The disclosed illustrative embodiment of the invention uses coal as the primary carbonaceous feed. It is understood, however, that other solid or liquid carbonaceous feeds such as tar sands, shale, peat and heavier petroleum fractions, such as atmospheric and vacuum residuals, may be mixed with or replace the coal. Types of coal preferred for use as a feed in the system of the present invention includes the bituminous and sub bituminous and lignite. Anthracite coal is less preferred. Syngas for the indirect conversion steps is generated by gasification of coal in the gasifier 107 and the gasification of biomass in the gasifier 109. Additional syngas is generated from natural gas in the methane-steam reforming unit 111.

In the coal gasification step 107, a feedstock including coal, water and oxygen is converted to syngas having an $H_2/CO$ ratio of about 0.5 and $CO_2$, by means of conventional partial oxidation. In the biomass gasification step 109, biomass is converted to syngas having an $H_2/CO$ ratio of about 2 or more and $CO_2$, preferably by means of initial hydro-gasification and partial oxidation of the residual. In the step 111 of producing syngas from a feedstock including natural gas and water is converted into syngas having an $H_2/CO$ ratio of about 2.0. Preferably, the syngas provided to the methanol synthesis and the FT synthesis steps 101 and 103 has an $H_2/CO$ ratio of about 2.0.

There are several commercial systems available for separating hydrogen from carbon monoxide. Pressure swing adsorption (PSA) processes rely on the fact that under pressure, gases tend to be attracted to solid surfaces, or "adsorbed". The higher the pressure, the more gas is adsorbed; when the pressure is reduced, the gas is released, or desorbed. PSA processes can be used to separate gases in a mixture because different gases tend to be attracted to different solid surfaces more or less strongly. Syngas mixtures of H2, CO and CO2 can be separated by PSA to produce streams rich in hydrogen. Alternatively, syngas can be first subjected to water gas shift to produce a binary mixture of H2 and CO2 which can be separated by PSA or by other means known in the art such as membrane separation (where H2 permeates much more effectively than $CO_2$ to generate pure hydrogen streams). Finally active metal membranes of palladium and other related metal alloys may be used to separate hydrogen from other gases and commercially available options have been produced. U.S. Pat. Nos. 5,792,239, 6,332,913 and 6,379,645, and published applications Nos. US2003/3190486 and US2009/0000408 describe various ones of such separation techniques and are hereby incorporated by reference in their entireties.

In the step 101 of synthesizing methanol from syngas, syngas from the previously described steps is used as a feedstock to produce methanol and carbon dioxide. In the FT synthesis step 103, syngas is used as a feedstock to produce hydrocarbon products, and carbon dioxide. Tail gas containing unreacted CO and $H_2$ from the FT synthesis step 103 can be added to the DCL feeds for supplying additional reactants.

In the direct coal liquefaction step 105, a feedstock including coal, water and solvent or hydrogen donor solvent is converted to liquid products in a hydrogen containing atmosphere, during which by-product ammonia is also generated. $H_2$-rich gas separated from the syngas obtained from coal gasification step 107, the biomass gasification step 109 and/or the step 111 of producing syngas from natural gas, is supplied to the direct coal liquefaction step 105 in order to increase efficiency and productivity of the direct coal liquefaction process. Tail gas of the FT synthesis step 103 includes unreacted CO and/or $H_2$ and is also used in the direct coal liquefaction step 105. Residue from the direct coal liquefaction step 105 is mixed with the biomass or biomass residue supplied to the gasifier 109 for conversion into additional syngas.

The biomass supplied to the gasification step 109 may be wood, straw, corncob, algae, residue from pyrolysis or hydrolysis of wood or the like, any other plant-derived material, or combinations thereof. Algae is a particularly advantageous source of part or all of such biomass because it can be produced on site using $CO_2$ produced in the various steps of the ICTL process of the invention, thereby substantially reducing the GHG emissions and increasing the carbon efficiency of the process. The other described sources of biomass also remove $CO_2$ from the atmosphere by photosynthesis during their growth processes, and so their use is also considered to reduce the GHG effluent from the ICTL process of the invention.

In accordance with an important aspect of the method of the invention, the GHG emissions, such as $CO_2$, from the ICTL facility of the invention are substantially reduced, and the carbon efficiency is increased by using much of the $CO_2$ to produce useful chemicals, in the illustrated embodiment, dimethyl carbonate (DMC). In the illustrated embodiment, $CO_2$ produced by the previously described steps is recovered and reacted with ammonia in a urea synthesis step 113 to produce urea. The $CO_2$ recovery can be conducted using various conventional recovery processes including, but not limited to, adsorption, absorption (e.g. pressure swing adsorption (PSA) and displacement purge cycles (DPC)), cryogenic separation, membrane separation, combinations thereof and the like. While one or more recovery processes may be needed to recover $CO_2$ from syngas or tail gas, by-product gas from a reformer or C3+ product upgrader will not contain appreciable amounts of $H_2$ or $H_2O$ and thus may not need any recovery process except for condensation of heavy hydrocarbons (C6+). Additionally, while it is desirable to use recovered $CO_2$ in processes of the present invention, it is also possible to supplement or replace recovered $CO_2$ with $CO_2$ obtained from alternative sources within an integrated complex.

Urea produced by the urea synthesis step 213 is then reacted with methanol produced by the methanol synthesis step 101 in the DMC synthesis step 115 to produce DMC and ammonia. Ammonia produced in the DMC synthesis step 115 and/or byproduct ammonia from the direct coal liquefaction step 105 is used as the reactant ammonia in the urea synthesis step 113.

DMC is particularly useful as an additive in transportation fuels in that it has high octane, about 105, and can be used as an additive in gasoline, and when used as an additive in diesel fuel, it substantially reduces the GHG emissions produced by the combustion of the diesel as a transportation fuel. For example, an addition of 2% of DMC to diesel fuel has been found to reduce soot emissions from a diesel powered vehicle by as much as 20%. DMC has the further unique advantage among chemicals useful as fuels or fuel additives, that it's molecular H2/CO ratio is 1/1, and thus reduces the overall stoichiometric H2/CO ratio for the ICTL facility.

Product streams from the process of the present invention can include, for example, a synthetic crude and other individual product streams such as liquefied petroleum gas (C3-C4), condensate (C5-C6), high-octane blend components (C6-C10 aromatic-containing streams), jet fuel, diesel fuel, other distillate fuels, lube blend stocks or lube blend feedstocks that can be produced and sold as separate products.

FT Synthesis

Reactors, catalysts and conditions for performing FT synthesis are well known to those of skill in the art and are described in numerous patents and other publications, for example, in U.S. Pat. Nos. 7,198,845, 6,942,839, 6,315,891, 5,981,608 and RE39,073, the contents of which are hereby incorporated by reference in their entirety. FT synthesis can be performed in fixed bed, moving bed, fluid bed, ebulating bed or slurry reactors using various catalysts and under various operating conditions that are selected based on the desired product suite and other factors. Typical FT synthesis products include paraffins and olefins, generally represented by the formula $nCH_2$. The productivity and selectivity for a given product stream is determined by reaction conditions including, but not limited to, reactor type, temperature, pressure, space rate, catalyst type and syngas composition.

The stoichiometric syngas $H_2/CO$ ratio for FT synthesis is about 2.0. The ratio of $H_2/CO$ in syngas produced from coal is less than 2, and typically about 0.5. This ratio can be increased by mixing the coal produced syngas with syngas produced from biomass or natural gas. If such mixing step does not increase the $H_2/CO$ ratio adequately, and additional hydrogen is not conveniently available from other sources, such ratio may be further increased by the water-gas shift reaction. In the case of FT synthesis conversion performed using a cobalt-based catalyst, which does not a promote water-gas shift reaction, the $H_2/CO$ ratio of coal produced a syngas is preferably increased to about 2.0 before being introduced in the FT synthesis reactor by reacting a portion of the syngas with steam in a shift converter (not shown) to generate additional hydrogen and $CO_2$. If the FT synthesis conversion is being performed using an iron-based catalyst, which does provoke the water-gas shift reaction, it is not necessary to use a separate shift converter. In either case, however, the water-gas shift reaction generates additional $CO_2$.

Direct Coal Liquefaction

Figure 2:
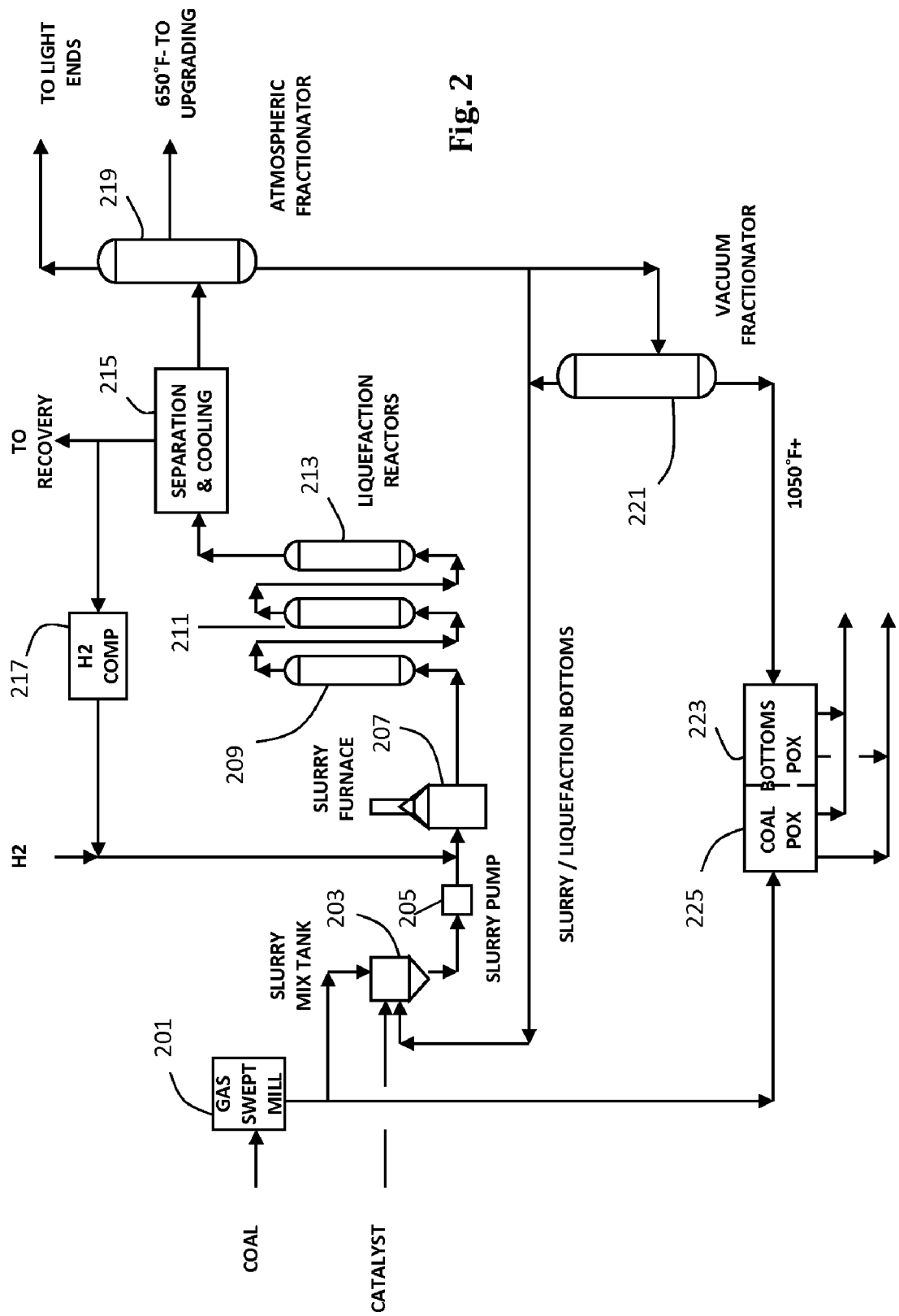
FIG. 2 is a schematic diagram of a direct coal liquefaction system in accordance with the invention.

An illustrated embodiment of a system in accordance with the invention for performing the direct coal liquefaction 105 (FIG. 1) is shown in FIG. 2 of the drawings. The coal feed is dried and crushed in a conventional gas swept roller mill 201 to a moisture content of 1 to 4%. The crushed and dried coal is fed into a mixing tank 203 where it is mixed with a solvent containing recycled bottoms and a catalyst precursor to form a slurry stream. The catalyst precursor in the illustrated embodiment preferably is in the form of the 5-10% aqueous water solution of phosphomolybdic acid (PMA) in an amount that is equivalent to adding between 50 wppm and 2% molybdenum relative to the dry coal feed.

The slurry leaves the mixing tanks at about 300 to 500° F. (139 to 260° C.). Most of the moisture in the coal and the water in the PMA feed are driven off in the mixing tank due to the hot recycle solvent (650/1000° F. or 353/538° C.) and bottom feeding to the mixing tanks. Such moisture and entrained volatiles are condensed out as sour water (not shown in FIG. 2). The coal in the slurry leaving the mixing tanks has about 0.1 to 1.0% moisture. The coal slurry is pumped from the mixing tanks and the pressure raised to about 2,000 to 3,000 psig (138 to 206 kg/cm² g) by the slurry pumping system 205. The resulting high pressure slurry is preheated in a heat exchanger (not shown), mixed with hydrogen, and then further heated in furnace 207.

The coal slurry and hydrogen mixture is fed to the input of the first stage of the series-connected liquefaction reactors 209, 211 and 213 at about 600 to 700° F. (343° C.) and 2,000 to 3,000 psig (138 to 206 kg/cm² g). The reactors 209, 211 and 213 are up-flow tubular vessels, the total length of the three reactors being 50 to 150 feet. The temperature rises from one reactor stage to the next as a result of the highly exothermic coal liquefaction reactions. In order to maintain the maximum temperature in each stage below about 850 to 900° F. (454 to 482° C.), additional hydrogen is preferably injected between reactor stages. The hydrogen partial pressure in each stage is preferably maintained at a minimum of about 1,000 to 2,000 psig (69 to 138 kg/cm² g).

The effluent from the last stage of liquefaction reactor is separated into a gas stream and a liquid/solid stream, and the liquid/solid stream let down in pressure, in the separation and cooling system 215. The gas stream is cooled to condense out the liquid vapors of naphtha, distillate, and solvent. The remaining gas is then processed to remove $H_2S$ and $CO_2$ Most of the processed gas is then sent to the hydrogen recovery system 17 for further processing by conventional means to recover the hydrogen contained therein, which is then recycled to be mixed with the coal slurry. The remaining portion of the processed gas is purged to prevent buildup of light ends in the recycle loop. Hydrogen recovered therefrom is used in the downstream hydro-processing system.

The depressurized liquid/solid stream and the hydrocarbons condensed during the gas cooling are sent to the atmospheric fractionator 219 where they are separated into light ends, naptha, distillate and bottoms fractions. The light ends are processed to recover hydrogen and $C_1$-$C_4$ hydrocarbons that can be used for fuel gas and other purposes. The naphtha is hydrotreated to saturate diolefins and other reactive hydrocarbon compounds. The 160° F.+ fraction of the naptha can be hydrotreated and powerformed to produce gasoline. The distillate fraction can be hydrotreated to produce products such as diesel and jet fuel.

The atmospheric fractionator 219 is preferably operated at a high enough pressure so that a portion of the 600 to 700° F.+ (315 to 371° C.+) bottoms fraction can be recycled to the slurry mixing tank 203 without pumping for use as the solvent. Pumping of this stream would be difficult because of its high viscosity and high solids content.

The remaining bottoms produced from the atmospheric fractionator 219 are fed to the vacuum fractionator 221 wherein it is separated into of 1000° F.− fraction and a 1000° F.+ fraction. The 1000° F.− fraction is added to the solvent stream being recycled to the slurry mix tank 203. The 1000° F.+fraction is fed to the bottoms partial oxidation gasifier 223 where it is reacted with oxygen to produce hydrogen and $CO_2$ by means of partial oxidation and water-gas shift reactions. If additional hydrogen is needed for the direct coal liquefaction and upgrading of the products thereof, a portion of the coal from the gas swept roller mill 201 is fed to the coal partial oxidation gasifier 225 for producing the additional required hydrogen. The ash resulting from the partial oxidation of the 1000° F.+ fraction and of the coal in the gasifiers 223 and 225 can be can be sent to the landfill or can be used to produce construction materials such as cement bricks, road surface paving material and other construction applications.

If the coal being converted by DCL is lignite, which has a higher $H_2O$ and $O_2$ content than bituminous or sub-bituminous coal, it is preferred to pre-treat the coal in an aqueous carbon monoxide-containing environment, as described in U.S. Pat. No. 5,026,475, the disclosure of which is hereby incorporated by reference in its entirety.

If the DCL process is being operated with relatively low catalyst concentrations of about 50 wppm to 500 wppm, in which about 70 to 80% of the input coal is converted to products, it is economically preferable to recycle only the portions of the catalyst that are entrained in the solvent stream being fed back to the slurry mix tank 203. At higher catalyst concentrations of about 1 to 5 wt %, in which about 80 to 95% of the input coal is converted to products, it is preferred to recover the remaining catalyst from the ash produced by the bottoms partial oxidation 223 by a process such as the one described in U.S. Pat. No. 4,417,972 the disclosure of which is hereby incorporated by reference in its entirety.

An illustrative process for upgrading the liquid product of the direct coal liquefaction step 105 is disclosed in U.S. Pat. No. 5,198,099, the disclosure of which is hereby incorporated by reference in its entirety. In this upgrading process, liquid product from the DCL process is hydrotreated in three successive zones. In the first hydrotreating zone most of the hetero atoms are removed and light products, such as chemical and light hydrocarbon gases, naphtha and water are removed and separated. Chemical gases include $CO_2$, CO, $NH_3$ and $H_2$. In the subsequent zones the nitrogen level is reduced, preferably to less than about 25 ppm, and the resulting liquid is hydrocracked to yield products including ultra-pure distillates. Catalysts useful in DCL processes also include those disclosed in U.S. Pat. Nos. 4,077,867, 4,196,072 and 4,561,964, the disclosures of which are hereby incorporated by reference in their entirety.

Methanol Synthesis

The synthesis of methanol in methanol synthesis step 101 (FIG. 1) can be performed using standard commercially available technologies. Some suitable methanol synthesis methods are described in U.S. Pat. Nos. 4,339,413, 6,921,733 and 7,189,379, the disclosures of which are hereby incorporated by reference in their entireties.

Urea Synthesis

The synthesis of urea from a $CO_2$ and ammonia in the step 113 and can be performed by standard commercially available urea production technologies. The processes described in U.S. Pat. Nos. 5,096,599 and 5,359,140 are typically those that can be used in the practice of the present invention.

DMC Synthesis

In the illustrated embodiment, the catalytic reaction of urea and methanol to DMC is carried out in a catalytic rectification reactor (also referred to as a catalytic distillation reactor) with the catalyst loaded in the reaction section of the reactor, or alternatively in a moving bed reactor where the catalyst is physically transported through the reaction zone to allow better control of the reaction kinetics and equilibria of the process. A methanol solution of urea formed by dissolving urea in methanol enters the catalyst bed layer from the upper portion of the catalyst containing section, with the urea in the solution entering the catalyst bed layer while methanol in the solution enters the rectifying section of the catalytic rectification reactor due to higher temperature. The reaction raw material methanol enters catalyst bed layer from the lower portion of the catalyst containing section. Urea and the reaction raw material methanol react in the catalyst section to form DMC.

Alternatively, the DMC synthesis can be carried out in the catalytic rectification reactor in a method comprising: (1) dissolving urea in methanol to form a methanol solution of urea, in which weight percentage of urea is in a range of from 1% to 99%; (2) feeding the methanol solution of urea into the catalyst bed layer from upper portion of the catalyst section of the catalytic rectification reactor in a feeding rate of from 0.01 to 10 ml/gcat/min, and feeding reaction raw material methanol into the catalyst bed layer from lower portion of the catalyst section of the catalytic rectification reactor in a feeding rate of from 0.01 to 20 ml/gcat/min, wherein the reaction is carried out at conditions including reaction temperature of from 120° C. to 250° C., reaction pressure of from 0.1 MPa to 5 MPa, kettle bottom temperature of from 70° C. to 210° C., stripping section temperature of from 70° C. to 250° C., rectifying section temperature of from 70° C. to 280° C., and reflux ratio of from 1:1 to 20:1.

The weight percentage of urea in the methanol solution of urea is preferably in a range of from 20% to 50%. The feeding rate of the methanol solution of urea is preferably in a range of from 0.1 to 2 ml gcat./min. The feeding rate of the reaction raw material methanol is preferably in a range of from 0.1 to 10 ml/gcat/min. The reaction temperature is preferably in a range of from 150° C. to 200° C. The reaction pressure is preferably in a range of from 0.5 MPa to 3 MPa. The kettle bottom temperature is preferably in a range of from 110° C. to 180° C. The stripping section temperature is preferably in a range of from 150° C. to 190° C. The rectifying section temperature is preferably in a range of from 150° C. to 200° C. The reflux ratio is preferably in a range of from 1:1 to 6:1.

A suitable catalyst for the DMC synthesis step has a composition as follows: active component: from 20 to 50 wt %; and carrier: from 80 to 50 wt %. Materials that can be used as the carrier include, but are not limited to, active carbon, alpha-alumina, gamma-alumina, silica, molecular sieve or zeolite, and the like, or ceramic monolith supports that may be useful in a catalytic distillation reactor system.

The active component for the DMC catalyst can be selected from the group consisting of oxides and chlorides of alkali metals, alkali-earth metals and transition elements, and mixture thereof. The alkali metals include K, Na, Cs and Li. The alkali-earth metals include Ca and Mg. The transition elements include Zn, Pb, Mn, La and Ce.

The catalyst for DMC synthesis can be prepared by a method comprising the steps of: preparing an aqueous solution of soluble salt(s) of alkali metal, alkali-earth metal, or transition element according to the composition of the catalyst on a weight basis; adjusting the pH of the solution to 0-5 by KOH or NH3H2O etc.; spraying and impregnating the aqueous solution on a carrier (for example, by equal-volume spraying and impregnating process), to prepare an active component-supported carrier; drying the active component-supported carrier at a temperature of from 100° C. to 250° C. for 2 to 24 hrs; and finally calcining the dried active component-supported carrier at a temperature of from 500° C. to 1000° C. for 2 to 12 hrs.

Useful soluble metal salts include nitrates, acetates, oxalates, hydroxides, halides and the like of alkali metals, alkali-earth metals, and transition elements. The pH value is preferably adjusted to 1-3. The calcination temperature is preferably in a range of from 650° C. to 800° C. The calcination time is preferably in a range of from 4 to 8 hrs. In the course of the preparation of the catalyst, control of pH value of the aqueous solution, calcination temperature and calcination time are the key points.

U.S. Pat. No. 7,271,120 describes suitable methods for preparing catalysts for use in the DMC synthesis and is hereby incorporated by reference in its entirety. DMC synthesis methods are also described in: *High-Yield Synthesis of Dimethyl Carbonate from Urea and then Methanol Using a Catalytic Distillation Process, Ind. Eng. Chem. Res.* 2007, 46, 2683-2687, which is also hereby incorporated by reference.

Since a large part of $CO_2$ generated in the ICTL process is used to form DMC, $CO_2$ compression and sequestration steps are avoided or minimized, thereby increasing the overall thermal efficiency of the process. The use of $CO_2$ in the formation of DMC provides higher material efficiency to useful products and the combination of FT derived diesel together with DMC as a blended fuel provides significant emissions benefits for the combined products, allowing further reduction in the overall Greenhouse gas footprint of the plant.

In the integrated process 100, only a small amount of ammonia is actually consumed because the ammonia is recycled in the process. Therefore, there is no need to provide a large supplement of ammonia. Alternatively, the ammonia may be purchased commercially, or may be synthesized from nitrogen and hydrogen obtained from air separation.

The $CO_2$ emissions in the integrated coal-to-liquids process are studied hereafter by examining the stoichiometry of the reactions that occur in the integrated process. Two reactions that occur in the coal gasification step 101 include 1 mole of carbon reacting with 1 mole of water to yield 1 mole of carbon monoxide and 1 mole of hydrogen gas, according to the following reaction equation:

$$C+H_2O \rightarrow CO+H_2 \quad (a)$$

In the coal gasification step 101, 1 mole of carbon monoxide reacts with 1 mole of water to give 1 mole of carbon dioxide and 1 mole of hydrogen (the WGS reaction), according to the following reaction equation:

$$CO+H_2O \rightarrow CO_2+H_2 \quad (b)$$

In the methanol synthesis step 103, 1 mole of carbon monoxide reacts with 2 moles of hydrogen to give 1 mole of methanol, according to the following reaction equation:

$$CO+2H_2 \rightarrow CH_3OH \quad (c)$$

In the urea synthesis step 105, 2 moles of ammonia react with 1 mole of carbon dioxide (obtained from the WGS reaction) to give 1 mole of urea and 1 mole of water, according to the following reaction equation:

$$2NH_3+CO_2 \rightarrow urea+H_2O \quad (d)$$

In the DMC synthesis step 107, 2 moles of methanol react with 1 mole of urea (obtained from the urea synthesis step 105) to give 1 mole of DMC and 2 moles of ammonia (to be recovered and used in the urea synthesis step 105), according to the following reaction equation:

$$2CH_3OH+urea \rightarrow DMC+2NH_3 \quad (e)$$

According to the calculation of materials balance based on the above reactions, the carbon dioxide emission in the integrated coal-to-liquids process could theoretically be zero. Instead of synthesizing methanol from syngas, methanol could be purchased commercially depending on the price and availability at the time in question.

In an alternative embodiment of the present invention, additional hydrogen can be generated by reformation of naphtha produced in either or both of the FT synthesis conversion and direct liquefaction steps 103 and 105, respectively. Hydrogen generated during naphtha reformation can be used in the direct coal liquefaction, to increase the $H_2$/CO ratio of syngas, and can also be used for other processes such as, hydrotreating a portion of the C5+ product to remove olefins, oxygenates and other trace heteroatoms. Hydrogen is generated during naphtha reformation by converting at least a portion of C5+Fischer-Tropsch product into aromatics. A typical reaction for a $C_6$ paraffin is:

$$C_6H_{14} \rightarrow C_6H_6+4H_2$$

Aromatic products produced by the above naphtha reforming processes can be used in various applications including high octane blend components for gasolines, typically including a mixture of C6-C10 aromatics, benzene for use in chemicals, especially for use in the production of cyclohexane, ethylbenzene and/or cumene, toluene for use as a chemical and xylenes for use as chemicals, especially for the production of paraxylene.

The removal of hydrogen from a Fischer-Tropsch product causes the net C5+ products to have a lower hydrogen to carbon stoichiometric ratio. That is, even though the initial hydrogen to carbon ratio is about 2.0, after conversion of a portion of the product into aromatics, the hydrogen to carbon stoichiometric ratio of the C5+ products decline to a value less than about 2.0, preferably less than about 1.95, and more preferably less than about 1.90. For example, the hydrogen to carbon stoichiometric ratio of a C5+ product may decline to a value around 1.0 (e.g. benzene), or even less than 1.0 (e.g. naphthalene).

What is claimed is:

1. An integrated process for converting a coal containing feed to liquids comprising the steps of:
   a. converting a major portion of the coal containing feed to liquids by direct liquefaction and upgrading said liquids to produce distillate products;
   b. gasifying a minor portion of the coal containing feedstock to produce syngas;
   c. gasifying biomass to produce syngas;
   d. converting syngas produced by steps b and c to methanol;
   e. reacting $CO_2$ produced by one or more of the gasification steps with ammonia to form urea;
   f. reacting urea produced by step e with methanol produced by step c to produce dimethyl carbonate and ammonia; and
   g. using ammonia produced in step a and/or f as a reactant in step e.

2. The process of claim 1 wherein the syngas produced in step b has an H2/C0 ratio less than 2 and the syngas produced in step c has an H2/C0 ratio equal to or greater than 2.

3. The process of claim 1 further including the step of increasing the $H_2$/C0 ratio of the syngas produced by the gasification of the coal containing feedstock by the water-gas shift reaction.

4. The process of claim 1, further including increasing the $H_2$/C0 ratio of the portion of the syngas to be converted to methanol in step d to 2/1.

5. The process of claim 1 further including the step of converting syngas produced by steps b and c to hydrocarbon products by Fischer Tropsch synthesis.

6. The process of claim 4 wherein $CO_2$ produced by the Fischer Tropsch synthesis is included in the $CO_2$ reacted in step e to form urea.

7. The process of claim 4 wherein the feed to the direct coal liquefaction of step a includes hydrogen from the syngas produced by steps b and c.

8. The process of claim 1 wherein the feed into the biomass gasification of step c includes coal residue produced by the direct coal liquefaction of step a.

9. The process of claim 1 wherein said biomass includes algae.

10. The process of claim 1 further including the step of hydro-processing algae to produce a liquid product and wherein said biomass includes residue of the hydro-processed algae.

11. The process of claim 8 further including using $CO_2$ produced in the integrated process in the production of algae by photosynthesis.

12. The process of claim 10 further including using a portion of the urea produced in step e as a nutrient in the production of algae by photosynthesis.

13. The process of claim 8 wherein the algae is gasified by hydro-gasification to form a syngas having a. $H_2/CO$ ratio greater than 2.

14. The process of claim 11 including storing a portion of the urea produced in step e during time periods when algae production rate is reduced and using the stored urea as a nutrient for the production of algae during time periods when the algae production rate is increased.

15. A process for converting a coal containing feed to liquids comprising the steps of:
 a. converting at least a major portion of the coal containing feed to liquids by direct liquefaction and upgrading said liquids to produce distillate products;
 b. gasifying biomass to produce syngas;
 c. converting syngas produced by step b to liquids;
 d. increasing the hydrogen content of the feed in step a by supplementing said feed with hydrogen in the syngas produced in step b;
 e. reacting $CO_2$ produced by one or more of the above steps and water to form algae by photosynthesis;
 f. hydro-processing algae produced in step e to form hydrocarbons; and
 g. using algae residue produced by the hydro-processing in step f as biomass in step b.

16. The method of claim 15 wherein step a includes supplementing the hydrogen content of the feed with hydrogen produced by gasifying coal.

17. The method of claim 15 wherein the step of converting syngas to liquids includes converting said syngas to methanol.

18. The method of claim 17 wherein step a also produces ammonia, and further including the step of converting at least a portion of said methanol and said ammonia to urea.

19. The process of claim 18 further including using at least a portion of said urea as a nutrient in the production of said algae.

20. The method of claim 15 further including the step of gasifying a minor portion of said coal containing feed to produce syngas, wherein said coal containing feed produced syngas is included in the syngas converted in step c.

21. The method of claim 15 further including the step of gasifying natural gas to produce syngas, wherein said natural gas-produced syngas is included in the syngas converted in step c.

22. The method of claim 18 further including reacting at least a portion of said urea with at least a portion of said methanol to produce dimethyl carbonate and ammonia, and using at least a portion of said ammonia produced from said urea and methanol to produce said urea.

23. A process for converting a carbonaceous feed to liquids comprising the steps of:
 a. converting at least a major portion of the carbonaceous feed to liquids by direct liquefaction and upgrading said liquids to produce distillate products;
 b. gasifying an algae or algae residue containing biomass feed to produce syngas;
 c. converting syngas produced by step b to liquids;
 d. increasing the hydrogen content of the feed in step a by supplementing said feed with hydrogen in the syngas produced in step b;
 e. producing algae by photosynthesis using $CO_2$ produced by one or more of the above steps; and
 f. supplying algae produced in step e, or algae residue produced by hydroprocessing algae produced in step e, as algae or algae residue containing biomass feed in step b.

24. The method of claim 23 wherein step a includes supplementing the hydrogen content of the feed with hydrogen produced by gasifying a minor portion of said carbonaceous feed.

25. The method of claim 23 wherein the step of converting syngas to liquids includes converting said syngas to methanol.

26. The method of claim 25 wherein step a also produces ammonia, and further including converting at least a portion of said methanol and said ammonia to urea and using at least a portion of said urea as a nutrient in the production of said algae.

* * * * *